(12) United States Patent
Toyama et al.

(10) Patent No.: US 6,660,005 B2
(45) Date of Patent: Dec. 9, 2003

(54) VERTEBRA CORRECTING AND FIXING DEVICE

(75) Inventors: Yoshiaki Toyama, Tokyo (JP); Morio Matsumoto, Tokyo (JP); Takashi Nishizawa, Tokyo (JP); Hirokazu Amino, Kyoto (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 10/034,211

(22) Filed: Dec. 26, 2001

(65) Prior Publication Data

US 2002/0082601 A1 Jun. 27, 2002

(30) Foreign Application Priority Data

Dec. 27, 2000 (JP) ........................................ 2000-398634

(51) Int. Cl.[7] ................................................ A61B 17/56
(52) U.S. Cl. .............................. 606/61; 606/60; 606/72; 606/73
(58) Field of Search ................................ 606/61, 60, 53, 606/54, 69, 70, 71, 72, 73

(56) References Cited

U.S. PATENT DOCUMENTS 5,176,680 A    1/1993   Vignaud et al.

Primary Examiner—Cary E. O'Connor
Assistant Examiner—Candice C. Melson
(74) Attorney, Agent, or Firm—Hogan & Hartson

(57) ABSTRACT

A vertebra correcting and fixing device including: a vertebra fixing screw to be threadedly connected to a vertebra; A movable spherical body which can be combined with this vertebra fixing screw; and a clamping screw threadedly connected to the movable spherical body. The movable spherical body is substantially spherical, has a split through-hole formed in the diametrical direction thereof, and also has a screw hole extending at right angles to tho split through hole and communicating therewith. Provision is made such that the clamping screw is threadedly connected to this screw hole. The vertebra fixing screw is provided at one end thereof with a threaded portion and at the other end thereof with a groove-shape scat portion for receiving and holding the movable spherical body. The seat portion is capable of rotatably holding the spherical body.

11 Claims, 4 Drawing Sheets

VERTEBRA CORRECTING AND FIXING DEVICE

BACKGROUND OF THE INVENTION

1. Field of the Invention

The present invention relates to a vertebra correcting and fixing device to be used for holding a vertebra in a desired spatial arrangement.

2. Description of Related Art

To correct vertebras, there has conventionally been conducted a correcting operation using a rod and three or more vertebra correcting and fixing devices each having a vertebra fixing screw. According to such a correcting operation, the vertebra fixing screws are threaded into the pedicles of vertebrae to connect the vertebra correcting and fixing devices to the vertebrae, and the vertebra correcting and fixing devices are joined to one another by the rod. Then, the rod is suitably deformed to fix the vertebrae in a desired arrangement.

As prior art, the U.S. Pat. No. 5,176,680 discloses a vertebra correcting and fixing device to be used in such a correcting operation. The arrangement of this Vertebra correcting and fixing device is shown in FIG. 4 in the present application. This vertebra correcting and fixing device 20 is arranged such that a rod B is attached into a vertebra fixing screw 22 provided at the top thereof with a U-shape seat portion 21. The device 20 comprises a clamping screw 23 and a split ring 24 threadedly connected to the upper side of the seat portion 21. With the rod B inserted into the split ring 24, the split ring 24 is fixed between the clamping screw 23 and a bottom surface 25 of the seat portion 21.

The split ring 24 is provided on the outer peripheral surface thereof with a spherical convex surface. When the clamping screw 23 is loosened, this outer peripheral surface can come in sliding contact with the bottom surface 25 of the seat portion 21. This enables the rod B to be adjusted in direction.

When the clamping screw 23 is fastened, the outer peripheral surface of the split ring 24 not only comes in contact with both a complementary spherical concave surface formed at the head (lower portion) of the clamping screw 23 and a complementary spherical concave surface formed in the inner wall surface of the seat portion 21 of the vertebra fixing screw 22, but also comes in pressure contact with the bottom surface 25 of the seat portion 21. This regulates the movement of the split ring 24 and also the movement of the rod B inserted thereinto.

When the split ring 24 is moved with the clamping screw 23 fastened, the rod B is changed in direction to loose the vertebra correcting effect. Therefore, the split ring 24 should securely be fixed with a large fixing force.

According to the arrangement of the prior art above-mentioned, however, the split ring 24 is merely held and fixed by the clamping screw 23 between the same and the bottom of the seat portion 21. Therefore, the split ring 24 fixing force is not sufficient. This involves the likelihood that the split ring 24 is moved when a large stress is exerted to the rod B even though the clamping screw 23 is fastened.

Further, according to the prior art above-mentioned, the clamping screw 23 can be fastened only in the axial direction of the vertebra fixing screw 22. Accordingly, if an obstacle is present in the axial direction of the vertebra fixing screw 22, this makes it difficult or impossible to fasten the clamping screw 23.

Further, according to the prior art above-mentioned, since the split ring 24 comes in contact with the bottom surface 25 of the seat portion 21, the movable range of the rod B is disadvantageously small. More specifically, when vertically rotating the rod B in the axial direction of the vertebra fixing screw 22, the inclination of the rod B at the time when the rod B comes in contact with the ridgeline of the bottom surface 25 of the seat portion 21, is relatively small.

SUMMARY OF THE INVENTION

It is a first object of the present invention to provide a vertebra correcting and fixing device in which the rod direction is adjustable and which can securely regulate the movement of the rod after the rod has been fixed.

It is a second object of the present invention to provide a vertebra correcting and fixing device in which, even when an obstacle is present in the axial direction of the vertebra fixing screw, the rod fixing operation can successfully be conducted while avoiding this obstacle.

It is a third object of the present invention to provide a vertebra correcting and fixing device in which the rod movable range is large, enabling the device to be applied to a greater number of cases.

According to the present invention, a vertebra correcting and fixing device comprises: a vertebra fixing screw to be threadedly connected to a vertebra; a movable spherical body which can be combined with the vertebra fixing screw; and a clamping screw threadedly connectable to the movable spherical body. The movable spherical body is substantially spherical, has a split through-hole formed in the diametrical direction thereof, and also has a screw hole extending at right angles to the split through-hole and communicating therewith. Provision is made such that the clamping screw is threadedly connected to this screw hole. The vertebra fixing screw is provided at one end thereof with a threaded portion and at the other end thereof with a groove-shape seat portion for receiving and holding the movable spherical body.

Preferably, the seat portion is capable of rotatably holding the spherical body.

According to the vertebra correcting and fixing device of the present invention, the split through-hole is preferably arranged such that a rod to be used for correcting a vertebra together with the device, can be inserted in the split through hole.

Preferably, the screw hole is arranged much that, when the clamping screw is fastened, the rod receives a pressing force from the clamping screw and is pushed to the inner wall surface of the split through hole in the movable spherical body, and that a pressing force from the rod causes the movable spherical body to receive force which tends to open and spread the slit of the split through-hole.

Preferably, the screw hole is formed in the spherical body at its position opposite to the slit of the split through-hole. Thus, a pressing force from the clamping screw can be transmitted to the rod, and a pressing force from the rod is exerted to the spherical body, causing the slit thereof to be spread or opened.

According to the present invention, when the clamping screw is fastened with the rod inserted into the split through-hole in the movable spherical body, the rod is pushed to the split through-hole for example at its bottom portion (at the split side). When the rod is moved to the narrower bottom portion of the split through-hole, the rod strongly pushes the wall surface of the bottom portion. Thus, the rod is fixed in the split through-hole in the movable spherical body, and the corresponding portions of the movable spherical body are pushed and spread outwardly. The portions thus spread of the movable spherical body are strongly pushed to the groove shape seat portion of the vertebra fixing screw. Accordingly, the reaction of the seat portion causes the movable spherical body to be securely fixed to the seat portion.

According to the vertebra correcting and fixing device of the present invention, the direction of the correcting rod can be adjusted and the direction once fixed can securely be maintained. This prevents the rod from being moved after the rod has been fixed. This eliminates the necessity of conducting an operation again, thus enhancing the safety.

Further, the spherical body to which the clamping screw is threadedly connected, is rotatable with respect to the seat portion of the vertebra fixing screw. This enables the screw hole to be turned in other direction than the axial direction of the vertebra fixing screw. It is therefore possible to select, out of a wide angular range, the working space for fastening the clamping screw. Accordingly, if there is an obstacle in the axial direction of the vertebra fixing screw, the clamping screw fastening working space can be assured in other direction than this axial direction. The clamping screw can therefore be fastened with good working efficiency. This enables the vertebra correcting and fixing device to be applied to a greater number of cases.

The seat portion may comprise a pair of opposing pieces which hold the spherical body thereby and therebetween. In this case, the end portion of the screw hole in the spherical body is preferably located as projecting from the two opposing pieces.

According to the arrangement above-mentioned, the opposing pieces are not an obstacle to the operation of fastening the clamping screw. Accordingly, the direction of the screw hole of the spherical body may be selected out of a wider angular range. This facilitates the clamping screw fastening operation.

Preferably, a gap is formed between the spherical body and the bottom surface of the seat portion. This increases the inclination of the rod at the time when the rod comes in contact with the ridgeline of the bottom surface of the seat portion when vertically rotating the rod in the groove-shape seat portion. This increases the movable range of the rod.

Preferably, the seat portion is provided at the bottom of the groove-shape thereof with a base portion, this base portion being provided at one or both ends of the groove-shape bottom with a spot-facing portion. According to such an arrangement, the rod vertical rotatable angular range can further be increased.

Preferably, the length of the spherical body along the split through-hole is shorter than its length along the direction at right angles to the split through-hole. Such an arrangement facilitates the assembling of the spherical body with the seat portion.

Preferably, the length of the spherical body along the split through-hole is shorter than the opening width of the groove-shape seat portion.

These and other features, objects, advantages and effects of the present invention will be more fully apparent from the following detailed description set forth below when taken in conjunction with the accompanying drawings.

DESCRIPTION OF THE PREFERRED EMBODIMENTS

Figure 1:
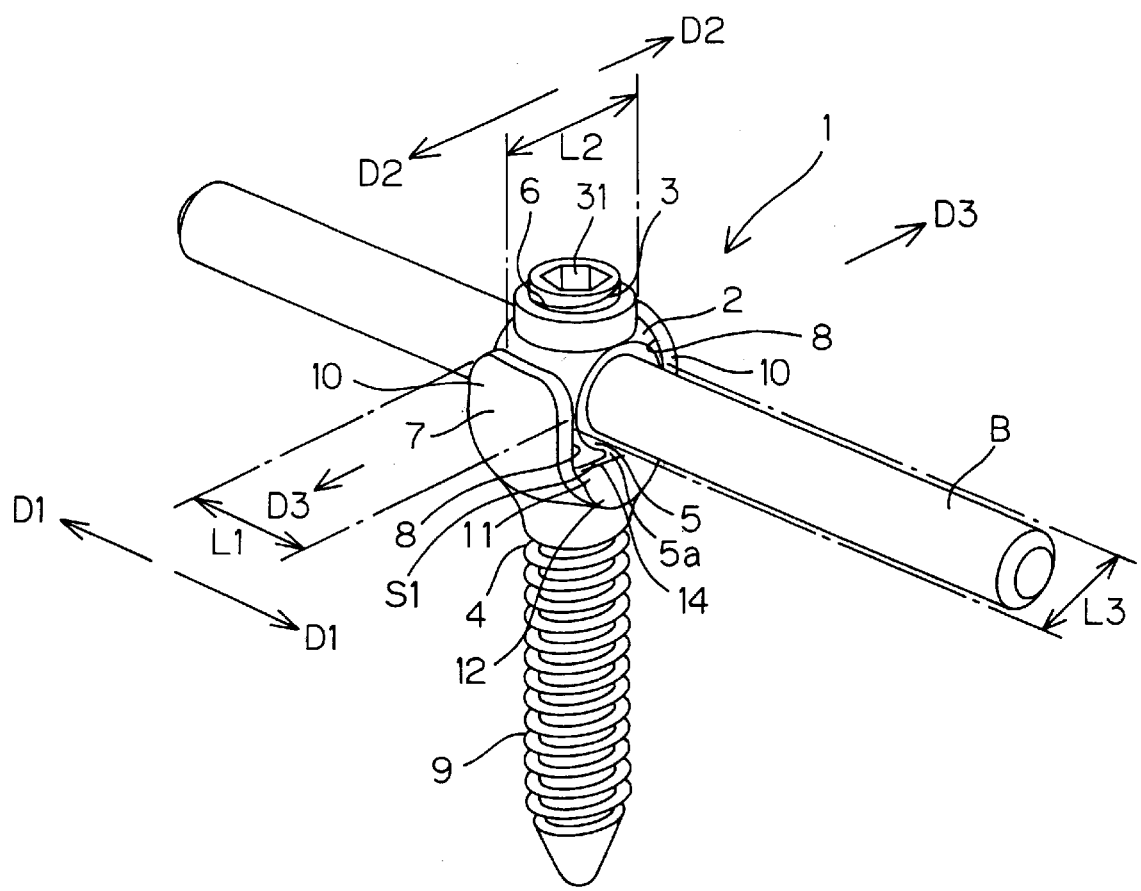
FIG. 1 is a perspective view of a vertebra correcting and fixing device according to an embodiment of the present invention, illustrating the state where the device is combined with a rod.
Figure 2:
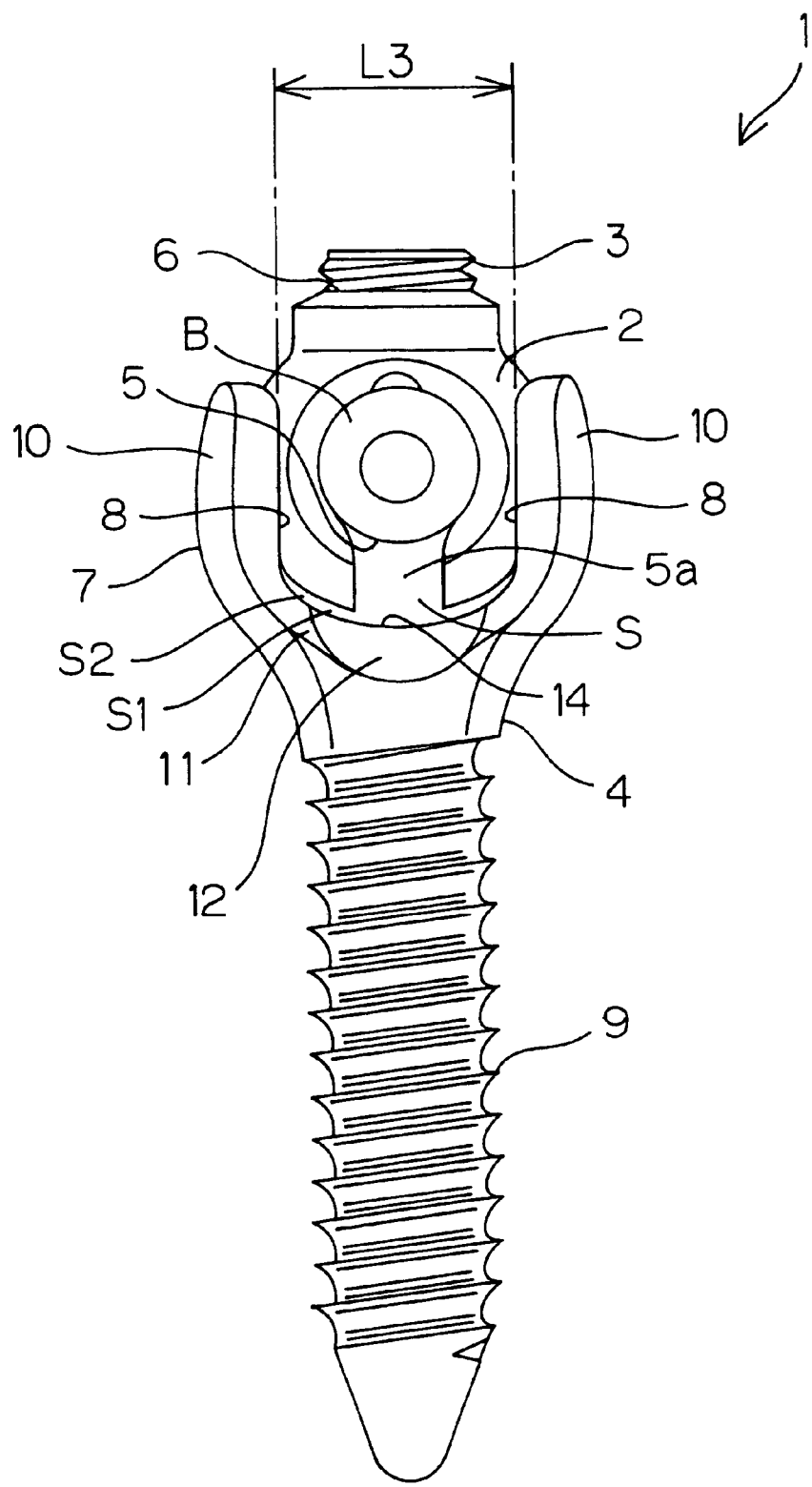
FIG. 2 is a front view of the vertebra correcting and fixing device in FIG. 1, illustrating the state where the clamping screw is not being fastened.
Figure 3:
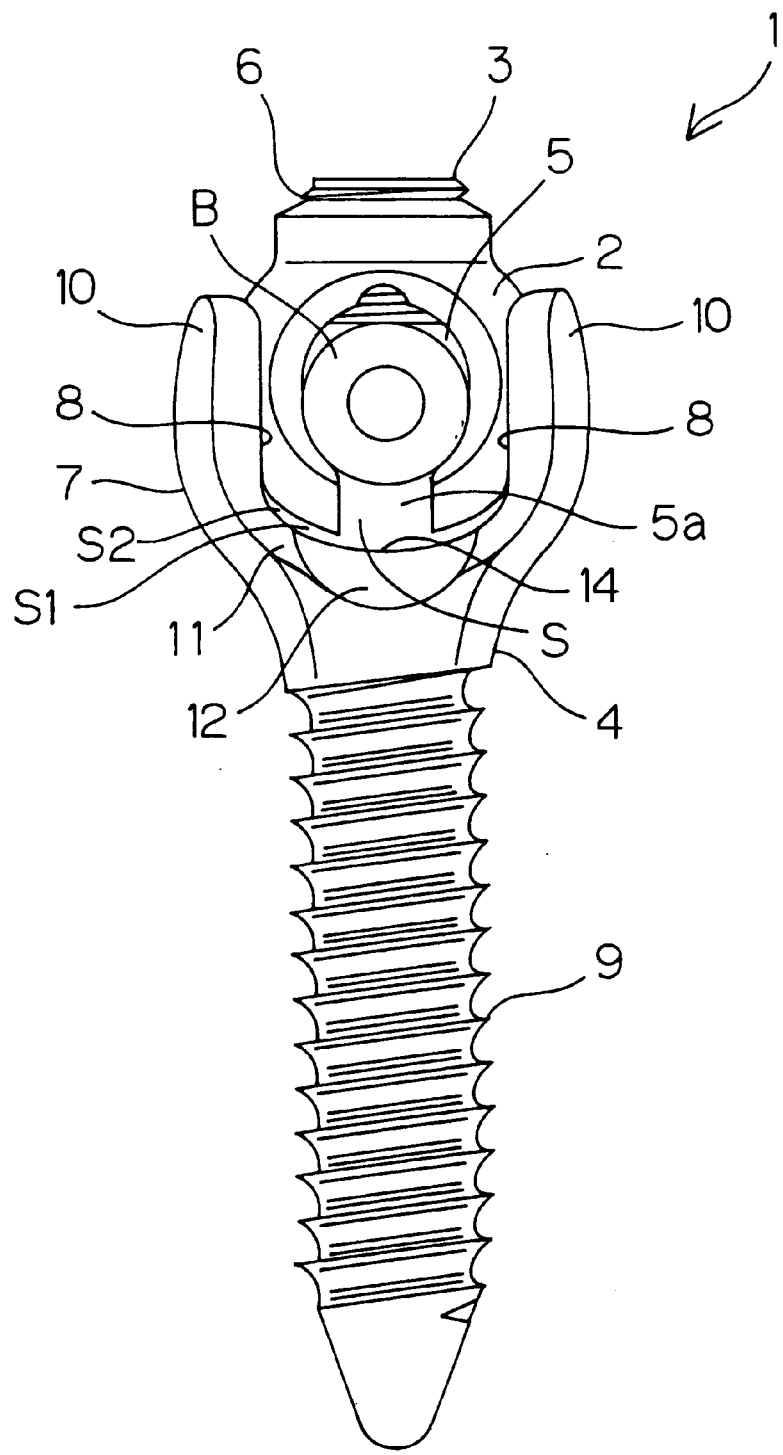
FIG. 3 is a front view of the vertebra correcting and fixing device in FIG. 1, illustrating the state where the clamping screw is fastened.
Figure 4:
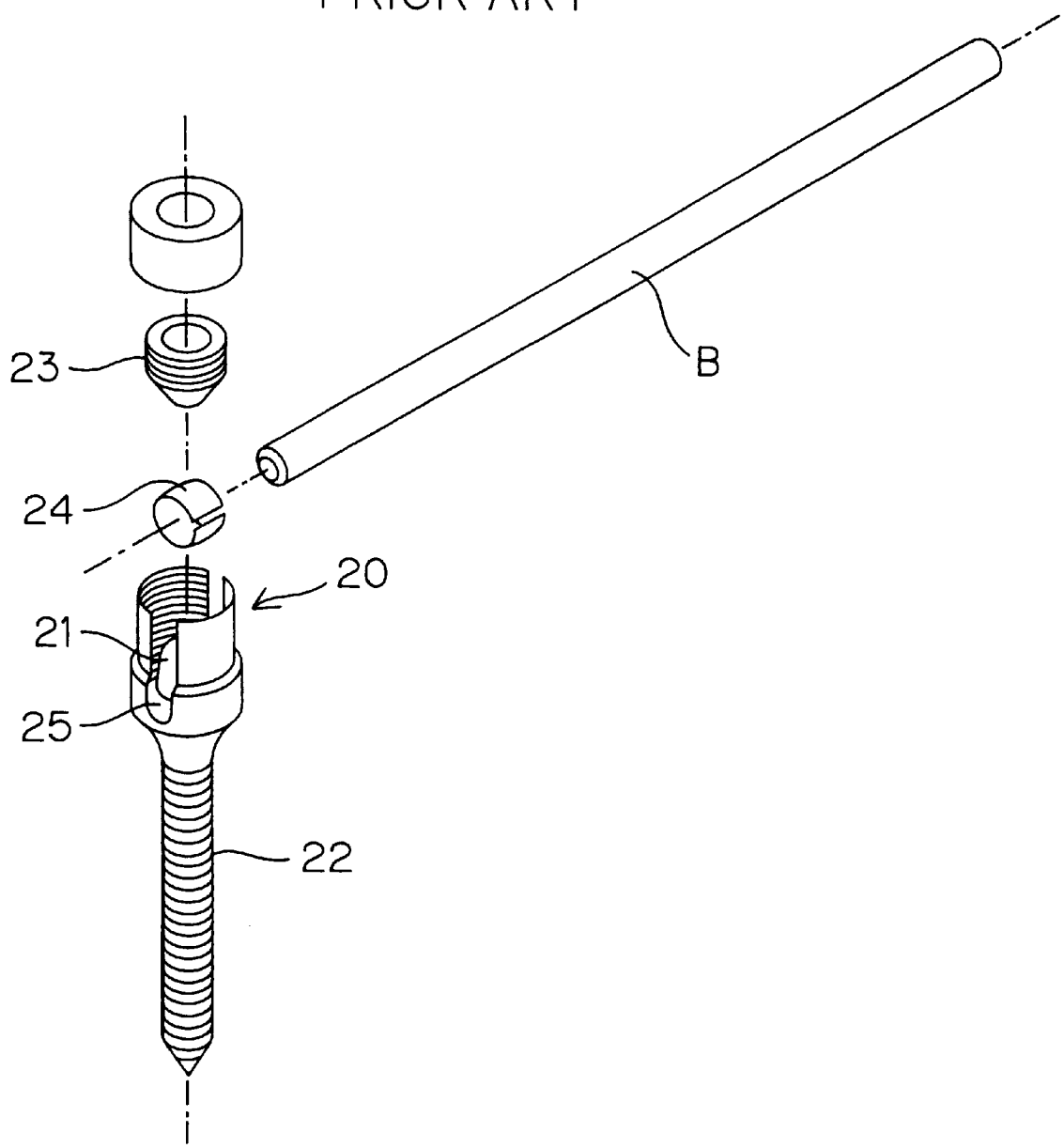
FIG. 4 is an exploded perspective view of a vertebra correcting and fixing device of prior art.

Referring to FIGS. 1 to 3, reference numeral 1 denotes a vertebra correcting and fixing device, reference numeral 2 denotes a movable spherical body, reference numeral 3 denotes a clamping screw, reference numeral 4 denotes a vertebra fixing screw, reference numeral 5 denotes a split through-hole, reference numeral 6 denotes a screw hole, reference numeral 7 denotes a seat portion, reference numeral 8 denotes spherical concave holding surfaces, reference numeral 9 denotes a threaded portion, and reference numeral 10 denotes opposing pieces. There is also shown a rod B for connecting a plurality of vertebra correcting and fixing devices 1 to one another.

The vertebra correcting and fixing device 1 is arranged such that the movable spherical body 2 is disposed on, as combined with, the vertebra fixing screw 4, and the clapping screw 3 is combined with the movable spherical body 2. The rod B can be joined to the movable spherical body 2.

The movable spherical body 2 is generally substantially spherical, and has thee split through-hole 5 and the screw hole 6. The split through-hole 5 is formed in a diametrical direction of the movable spherical body 2, and the screw hole 6 is formed at right angles to the split through-hole 5 and communicates therewith. The split through-hole 5 has a slit 5a of which width is narrower than the diameter of the rod B. The screw hole 6 is opened in the outer surface of the movable spherical body 2 at its upper side in FIGS. 2 and 3 opposite to the slit 5a.

The rod B for connecting a plurality of vertebra correcting and fixing devices 1 to one another, can be inserted into the split through-hole 5. A portion of a joint clamp (not shown) for holding the rod B, can also be inserted into the split through-hole 5.

The clamping screw 3 is threadedly connectable to the screw hole 6. A pressing force from the clamping screw 3 can act on the rod B inserted into the split through-hole 5. Thus, by fastening the clamping screw 3, the rod B can be fixed to the vertebra correcting and fixing device 1, as will be discussed later.

The clamping screw 3 is provided in one end thereof with a hexagonal hole 31. By fitting a hexagonal wrench in the hexagonal hole 31, the clamping screw 3 can be fastened.

The vertebra fixing screw 4 is provided at one end thereof with the threaded portion 9 and at the top on the other end thereof with the seat portion 7 which receives the movable spherical body 2. The seat portion 7 has a pair of opposing pieces 10 for holding the movable spherical body 2 therebetween, and also has a concave base portion 11. The opposing pieces 10 stand, as branched, from the base portion 11.

The two opposing pieces 10 are provided at the mutually opposite sides thereof with the spherical concave holding surfaces 8 for rotatably holding the movable spherical body 2. The bottom surface 14 of the base portion 11 is disposed between the spherical concave holding surfaces 8. Spot-facing portions 12 communicating with the bottom surface 14, are formed at both sides of the base portion 11 in the direction at right angles to the mutual opposing direction of the opposing pieces 10.

Provision is made such that a gap S2 (See FIGS. 2 and 3) is formed between the movable spherical body 2 and the bottom surface 14 of the base portion 11 when the spherical concave holding surfaces 8 holds the movable spherical body 2. On the other hand, the end portion of the screw hole 6 of the movable spherical body 2 is positioned as projecting from the two opposing pieces 10.

An shown in FIG. 1, those both ends of the movable spherical body 2 along the split through-hole 5 are cut and flattened. This, the length L1 of the movable spherical body 2 in the small-diameter direction D1-D1 along the split through-hole 5, is shorter than the length L2 of the movable spherical body 2 in the large-diameter direction D2-D2 horizontally perpendicular to the small-diameter direction D1-D1. The length L1 in the small-diameter direction D1-D1 is slightly smaller than the length L3 of a U-shape groove opening S1 of the seat portion 7.

According to the arrangement above-mentioned, the movable spherical body 2 can readily be mounted in a groove S between the opposing pieces 10 of the seat portion 7. More specifically, before the rod B is mounted, the small-diameter direction D1-D1 of the movable spherical body 2 along the split through-hole 5, is aligned with a direction D3-D3 at right angles to the groove S of the seat portion 7. This direction D3-D3 in parallel to a plane formed by the U-shape groove opening 51. The movable spherical body 2 in the posture above-mentioned is inserted in the groove S. The movable spherical body 2 can be inserted into the seat portion 7 because the length L3 of the groove S is larger than the length L1 in the small diameter direction D1-D1.

By rotating the movable spherical body 2 thus inserted, by 90° around the vertebra fixing screw 4, the movable spherical body 2 can be located such that its split through-hole 5 is opened in the U-shape groove opening S1 of the seat portion 7 as shown in FIGS. 2 and 3. Thus, the movable spherical body 2 is rotatably held in the seat portion 7, and the rod B can be inserted into the split through-hole 5 in the movable spherical body 2.

The following description will discuss how the vertebra correcting and fixing device 1 clamps the rod B.

FIGS. 2 and 3 are views illustrating the mode of fixing the rod B in the vertebra correcting and fixing device 1. FIG. 2 shows the state where the clamping screw 3 is not being fastened, while FIG. 3 shows the state where the clamping screw 3 has been fastened.

When the clamping screw 3 is fastened with the rod B inserted into the split through-hole 5 in the movable spherical body 2, the rod B receives a pressing force from the clamping screw 3. This causes the rod B to be pushed down from the position shown in FIG. 2 to the position shown in FIG. 3. When the rod B is moved to the narrower bottom portion of the split through-hole 5, the rod B strongly presses the wall surface of the bottom portion. Thus, the rod B is fixed in the movable spherical body 2, and those portions of the movable spherical body 2 corresponding to the rod B, are pushed and spread outwardly. More specifically, the movable spherical body 2 receives force which lends to open the slit 5a. The portions thus spread of the movable spherical body 2 strongly push the spherical concave holding surfaces 8 formed in the opposing pieces 10 of the vertebra fixing screw 4. Accordingly, the reaction of the spherical concave holding surfaces 8 causes the movable spherical body 2 to be securely fixed between the two opposing pieces 10.

According to such a mode of fixing the rod B and the movable spherical body 2 in the vertebra correcting and fixing device 1, a very large fixing force can be obtained by the pressing-spreading action of portions of the movable spherical body 2.

When the clamping screw 3 is loosened, the movable spherical body 2 is rotatable. Therefore, in the operation of fastening the clamping screw 3 with a hexagonal wrench, the operational direction can be selected in a wide angular range. Accordingly, if there is an obstacle in the axial direction of the threaded portion 9 of the vertebra fixing screw 4, the direction of the screw hole 6 of the movable spherical body 2 can be determined while avoiding the axial direction of the threaded portion 9. This assures a space for operation of fastening the clamping screw 3.

Further, the end of the screw hole 6 of the movable spherical body 2 is positioned as projecting from the opposing pieces 10. Accordingly, the opposing pieces 10 are not an obstacle to the operation of fastening the clamping screw 3. It is therefore possible to select the direction of the screw hole 6 in a wider angular range.

Further, the vertebra correcting and fixing device 1 is provided at the base portion 11 of the seat portion 7 with the spot-facing portions 12. Further, the vertebra correcting and fixing device has a gap S2 between the movable spherical body 2 and the bottom surface 14 of the seat portion 7, i.e., the bottom surface 14 of the base portion 11. This increases the inclination of the rod B at the time when the rod B comes in contact with the ridgeline of the bottom surface 14 of the seat portion 7 when vertically rotating the rod B in the groove S between the opposing pieces 10 of the seat portion 7. This increases the movable range of the rod B.

The following description will discuss a vertebra correcting operation using the vertebra correcting and fixing devices 1.

First, the vertebra fixing screw 4 is threadedly inserted in the podicle of each vertebra to be corrected. The rod B is suitably curved with a dedicated tool as necessary, and inserted in the split through-holes 5 in the movable spherical bodies 2 mounted on the vertebra fixing screws 4.

Next, to correct the vertebrae, a portion of the rod B thus mounted is lifted or bent with the use of a dedicated tool. At this time, because the movable spherical bodies 9 are movable in a relatively large directional range, the movable spherical bodies 2 can flexibly follow the movement of the rod B. This prevents an excessive stress from being exerted to the vertebra fixing screws 4.

Then, it is made sure that the rod B and the vertebra correcting and fixing devices 1 are properly arranged. Finally, the clamping screws 3 are fastened to fix the movable spherical bodies 2 to the vertebra fixing screw 4. This fixes the position of the rod B such that the vertebrae are maintained as corrected.

Embodiments of the present invention have been discussed in detail, but these embodiments are mere specific examples for clarifying the technical contents of the present invention. Therefore, the present invention should not be construed as limited to these specific examples. The spirit and scope of the present invention are limited only by the appended claims.

This Application corresponds to Japanese Patent Application Serial No. 2000-398634 filed on Dec. 27, 2000 with Japanese Patent Office, the disclosure of which is incorporated herein by reference.

What we claim is:

1. A vertebra correcting and fixing device comprising:
 a movable, substantially spherical body, which has a split through-hole formed in a diametrical direction thereof, and which also has a screw hole extending at right angles to the split through-hole and communicating therewith;
 a clamping screw threadedly connectable to the screw hole of the movable, substantially spherical body; and
 a vertebra fixing screw provided at one end thereof with a threaded portion and at the other end thereof with a groove-shape seat portion for receiving and holding the movable, substantially spherical body;
 wherein the movable, substantially spherical body is rotatable with respect to the seat portion of the vertebra fixing screw.

2. A vertebra correcting and fixing device according to claim 1, wherein the seat portion is arranged to rotatably hold the movable, substantially spherical body.

3. A vertebra correcting and fixing device according to claim 1, wherein the split through-hole is formed such that a rod is insertable therein.

4. A vertebra correcting and fixing device according to claim 3, wherein the screw hole is formed such that, when the clamping screw is fastened, the rod receives a pressing force from the clamping screw and is pushed to an inner wall surface of the split through-hole in the movable, substantially spherical body, and that a pressing force from the rod causes said movable, substantially spherical body to receive force which tends to spread and open a slit of the split through-hole.

5. A vertebra correcting and fixing device according to claim 1, wherein the screw hole is formed in the substantially spherical body at its position opposite to a slit of the split through-hole.

6. A vertebra correcting and fixing device according to claim 1, wherein the seat portion comprises a pair of opposing pieces which hold the substantially spherical body therebetween.

7. A vertebra correcting and fixing device according to claim 6, wherein an end portion of the screw hole in the substantially spherical body is located as projecting from the two opposing pieces.

8. A vertebra correcting and fixing device according to claim 1, wherein a gap is formed between the substantially spherical body and the bottom surface of the seat portion.

9. A vertebra correcting and fixing device according to claim 1, wherein the seat portion is provided at a bottom of the groove-shape thereof with a base portion,
 the base portion being provided at at least one end of the groove-shape with spot-facing portion.

10. A vertebra correcting and fixing device according to claim 1, wherein the substantially spherical body is arranged such that its length along the split through-hole is shorter than its length along a direction at right angles to the split through-hole.

11. A vertebra correcting and fixing device according to claim 10, wherein the length of the substantially spherical body along the split through-hole is shorter than the opening width of the groove shape seat portion.

* * * * *